United States Patent [19]

Wife et al.

[11] Patent Number: 4,720,589
[45] Date of Patent: Jan. 19, 1988

[54] BIS-PHOSPHINEOXIDE COMPOUNDS

[75] Inventors: Richard L. Wife; Johannes J. M. Snel; Aart B. Van Oort, all of Amsterdam, Netherlands

[73] Assignee: Shell Oil Company, Houston, Tex.

[21] Appl. No.: 26,923

[22] Filed: Mar. 17, 1987

Related U.S. Application Data

[62] Division of Ser. No. 797,549, Nov. 13, 1985, Pat. No. 4,683,338.

[30] Foreign Application Priority Data

Nov. 22, 1984 [GB] United Kingdom ................ 8429537

[51] Int. Cl.$^4$ .............................................. C07F 9/53
[52] U.S. Cl. ................................................. 568/15
[58] Field of Search ....................................... 568/15

[56] References Cited

U.S. PATENT DOCUMENTS

| | | | |
|---|---|---|---|
| 3,895,074 | 7/1975 | Mrowca | 260/606.5 |
| 3,975,447 | 8/1976 | Knoth, Jr. et al. | 260/606.5 |
| 4,365,094 | 12/1982 | Boileau et al. | 568/14 |
| 4,447,584 | 5/1984 | Bergeret al. | 525/340 |
| 4,565,892 | 1/1986 | Wife et al. | 568/14 |

OTHER PUBLICATIONS

Tetrahedron Letters 22 (1981), pp. 1875–1878.
Journal of General Chemistry of USSR, vol. 47, No. 11, part 2, Nov. 1977, p. 2390.

Primary Examiner—Helen M. S. Sneed

[57] ABSTRACT

A process for the preparation of phenylene-bis-phosphineoxide compounds by reacting in a polar aprotic solvent a difluorobenzene compound with a compound of the general formula

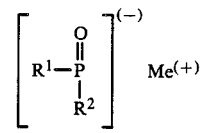

wherein Me is an alkali metal, $R^1$ and $R^2$ each independently represents an alkyl-, aryl-, alkaryl- or aralkyl group, or $R^1$ and $R^2$ together form an alkylene group.

4 Claims, No Drawings

BIS-PHOSPHINEOXIDE COMPOUNDS

This is a division of application Ser. No. 797,549, filed Nov. 13, 1985, now U.S. Pat. No. 4,683,338.

FIELD OF THE INVENTION

The present invention relates to a process for the preparation of phenylene-bis-phosphineoxide compounds and certain novel phenylene-bis-phosphineoxide compounds.

BACKGROUND OF THE INVENTION

Bis-phosphines are widely employed as bidentate ligands in transition metal catalyzed reactions. It is known to prepare bis-phosphines via reduction of bis-phosphineoxide precursors obtained by reaction of 1,2-ethanediyl bis-tosylates or epoxides with a secondary phosphineoxide reagent [cf.: Synthesis (1983) 71–73].

There is great interest in 1,2-phenylene-bis-phosphines as bidentate ligands for transition metals. However, their synthesis is difficult and thus hampers their wide application [cf.: Polyhedron 2 (1983) 303–304, Tetrahedron Letters 22 (1981) 1875–1878]. This is also true for the preparation of their usual precursors i.e. 1,2-phenylene-bis-phosphineoxides [cf.: Organometallics 2 (1983) 1877–1879].

SUMMARY OF THE INVENTION

The present invention relates to a process for the preparation of phenylene-bis-phosphineoxide compounds characterized in that in a polar aprotic solvent a difluorobenzene compound is reacted with a compound of the general formula

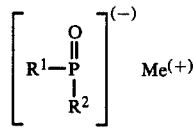

wherein Me is an alkali metal and $R^1$ and $R^2$ each independently represents an alkyl-, aryl-, alkaryl- or aralkyl group, or $R^1$ and $R^2$ together form an alkylene group.

DESCRIPTION OF THE PREFERRED EMBODIMENTS

Difluorobenzene compounds which can be used in the process of the invention may comprise 1,2-, 1,3-, or 1,4-difluorobenzene or substituted difluorobenzenes. They may carry substituents which comprise any group or element which does not interfere substantially with the reaction, such as hydroxy groups, alkyl groups, carboxylic acid groups, or chlorine.

Compounds of the general formula I wherein $R^1$ and/or $R^2$ represent an alkyl group in particular a tertiary alkyl group may suitably be used in the process of the invention. The use of secondary phosphineoxides of the general formula I wherein $R^1$ and/or $R^2$, and in particular $R^1$ and $R^2$, represent a phenyl group is preferred. The phenyl group $R^1$, $R^2$ may contain any substituent, which does not interfere with the reaction, ortho, meta or para to the site of attachment of the phosphorus atom, in particular an alkyl group or a group —$OR^3$ wherein $R^3$=H or an alkyl group, and preferably a tertiary alkyl group such as a tertiary butyl group.

The compounds of the general formula I should at least by partially soluble in the polar aprotic solvent. They may be prepared by reacting the corresponding secondary phosphineoxide of the general formula

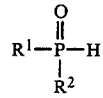

with a basic compound. Examples of suitable basic compounds are metal alkyl compounds such as butyl lithium and metal hydrides such as, for example, the aluminum hydride compound sodium dihydrobis(2-methoxyethanolato)aluminate or alkali metal hydrides, e.g. sodium hydride or lithium hydride. The basic compound is preferably reacted in an amount of 1 mol per mol of secondary phosphineoxide. The use of alkali metal hydrides is preferred.

Preferably, the compounds of the general formula I are prepared in-situ in a polar aprotic solvent. Suitable polar aprotic solvents for use in the process of the invention are preferably amides such as N,N'-dimethylformamide, N,N'-dimethylacetamide, N-methylpyrrolidone or 1,3-dimethyl-2-imidazolidinone. The use of N,N'-dimethylformamide is most preferred.

The reaction temperature may vary between ambient temperature and the boiling point of the reaction mixture. A temperature in the range of 80°–110° C. is preferred The phenylene-bis-phosphineoxide compounds obtained by the process of the invention can be reduced to bis-phosphines with good results by known silane reduction methods preferably employing phenylsilane.

Phenylene-bis-phosphineoxide compounds of the general formula

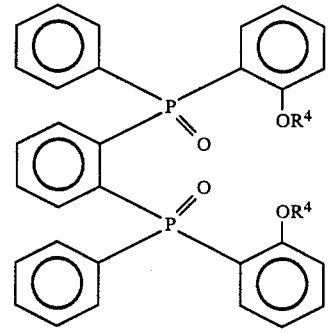

wherein $R^4$ represents H or an alkyl or aryl group are believed to be novel compounds. Examples of novel compounds according to the general formula III are 1,2-phenylene-bis-o-hydroxyphenylphenyl-phosphineoxide, 1,2-phenylene-bis-o-t-butoxyphenylphenyl-phosphine-oxide and 1,2-phenylene-bis-o-propoxyphenylphenylphosphineoxide. 1,2-Phenylene-bis-o-hydroxyphenylphenylphosphineoxide may in addition to its use as precursor to the corresponding bis-phosphine also be used in the preparation of phosphorus containing macrocycles [cf.: Izv. Akad. Nauk SSSR, Ser. Khim (1978) 1930–1932]. 1,2-Phenylene-bis(o-hydroxyphenylphenylphosphineoxide) is further very useful as a starting material for the preparation of derivatives, for example ethers or esters.

The process according to the invention is hereinafter illustrated using examples which are not to be construed as limiting the invention. In the following examples, the identities of the compounds have been determined by means of $^{13}$C and $^{31}$P NMR analysis.

EXAMPLE I

Preparation of 1,2-phenylene-bis-diphenylphosphineoxide

Sodium hydride (68 mmol, in the form of a 80% w/w suspension in mineral oil (Fluka)) was added to a stirred solution of diphenyl-phosphineoxide (68 mmol) in dry N,N'-dimethylformamide (120 ml) at room temperature under argon. With evolution of hydrogen, a yellow solution was formed. Then, o-difluorobenzene (33.9 mmol) was added and the mixture was warmed to 90° C. The yellow color gradually faded and after 9 hours the product mixture was cooled and acidified with dilute hydrochloric acid. The product was extracted with chloroform (500 ml), washed with sodium hydrogen carbonate and dried over magnesium sulfate. On evaporation of all chloroform, a colorless oil was obtained which after recrystallization with a dichloromethane diethylether mixture gave pure 1,2-phenylene-bis-diphenyl-phosphineoxide in 67% yield.

To demonstrate the easy conversion of this phosphineoxide into phosphine by reduction with phenylsilane, 1,2-phenylene-bis-diphenylphosphine oxide (3,95 mmol) was mixed with excess phenylsilane and the suspension was heated at reflux temperature (ca. 120° C.) for two days giving a homogeneous solution. After removal of excess, phenylsilane under high vacuum crystalline 1,2-phenylene-bis(diphenylphosphine) was obtained on addition of methanol in 88% yield.

EXAMPLE II

Preparation of 1,4-phenylene-bis-diphenylphosphineoxide

Sodium hydride (2.5 mmol, in the form of a 80% w/w suspension in mineral oil (Fluka)) was added to a stirred solution of diphenylphosphineoxide (2.5 mmol) in dry N,N'-dimethylformamide (10 ml) at room temperature under argon. With evolution of hydrogen a yellow solution was formed. Then, p-difluorobenzene (1.25 mmol) was added and the mixture was warmed to 140° C. The yellow color gradually faded and after 9 hours the product mixture was cooled and acidified with dilute hydrochloric acid. The product was extracted with chloroform (25 ml), washed with sodium hydrogen carbonate and dried over magnesium sulfate. On evaporation of all chloroform, the crude and almost pure product was obtained as a colorless oil (90%) which after recrystallization with a dichloromethane diethylether mixture gave pure 1,4-phenylenebis-diphenylphosphineoxide in 30% yield.

EXAMPLE III

Preparation of 1,2-phenylene-bis-o-hydroxyphenylphenylphosphineoxide

Sodium hydride (51.9 mmol, in the form of a 80% w/w suspension in mineral oil (Fluka)) was added to a stirred solution of (o-hydroxyphenyl)phenylphosphineoxide (24.7 mmol) in dry N,N'-dimethylformamide (150 ml) at room temperature under argon. The solution was added o-difluorobenzene (12.4 mmol) and then the mixture was heated at 95° C. over 5 hours. After cooling, the formed precipitate was filtered off, washed with diethylether and treated with dilute hydrochloric acid. Extraction with dichloromethane and partial evaporation of dichloromethane with concomitant addition of diethylether afforded 1,2-phenylene-bis-o-hydroxyphenylphenylphosphineoxide as a crystalline solid in 44% yield.

The residual solution contained another amount of 1,2-phenylene-bis-o-hydroxyphenylphenylphosphineoxide which was reacted with n-propylbromide as follows. All solvents of the residual solution were stripped and the residue was redissolved in acetone (100 ml). To this mixture were added n-propylbromide (50 ml) and potassium carbonate (10 g). The suspension obtained was refluxed overnight and filtered after cooling. The solvent was then evaporated and the resulting oil was dissolved in dichloromethane (minimal amount) and filtrated. On treating the dichloromethane solution with diethylether and standing overnight, 1,2-phenylene-bis-o-propoxyphenylphenylphosphineoxide was obtained as crystalline solid.

EXAMPLE IV

Preparation of 1,2-phenylene-bis-o-hydroxyphenylphenylphosphineoxide

Sodium hydride (36.5 mmol, in the form of a 80% w/w suspension in mineral oil (Fluka)) was added to a stirred solution of o-t-butoxyphenylphenylphosphineoxide (36.5 mmol) in dry N,N'-dimethylformamide (120 ml). After a yellow solution was obtained o-di-fluorobenzene was added and the reaction mixture was heated to 90°–100° C. over a period of 23 hours. The cooled reaction mixture was treated with aqueous ammonium chloride and the total mixture was extracted with dichloromethane (200 ml). After drying with magnesium sulfate and removing the solvent, an oil was obtained which on recrystallization with acetone yielded 1,2-phenylene-bis-o-t-butoxyphenylphenylphosphineoxide in 18% yield. A second portion of the product was obtained from the residue of the evaporation of the acetone mother liquor. The residue was dissolved in methanol (25 ml) stirred with a solution of $CuCl_2.2H_2O$ (2.7 g) in methanol (25 ml) for 15 minutes and diluted with diethylether (300 ml). The precipitate formed on standing of this mixture was treated with concentrated ammonium chloride and extracted with dichloromethane. From the dichloromethane solution obtained, 1,2-phenylene-bis-o-t-butoxyphenylphenylphosphineoxide was recovered in 23% yield following the same procedure as the dichloromethane solution of the first portion of the product. The total yield of product was 41%.

We claim as our invention:

1. Compounds of the general formula

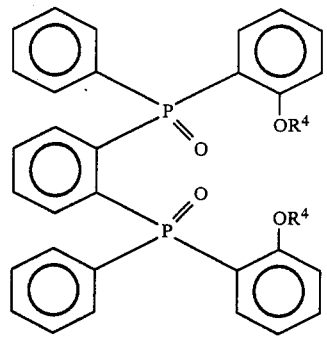
wherein $R^4$=H or an alkyl group with 1 to 4 carbons.
2. A compound according to claim 1 which is 1,2-phenylene-bis-o-hydroxyphenylphenylphosphineoxide.
3. A compound according to claim 1 which is 1,2-phenylene-bis-o-t-butoxyphenylphenylphosphineoxide.
4. A compound according to claim 1 which is 1,2-phenylene-bis-o-n-propoxyphenylphenylphosphineoxide.
* * * * *